(12) United States Patent
Chung et al.

(10) Patent No.: US 11,241,471 B2
(45) Date of Patent: Feb. 8, 2022

(54) **PHARMACEUTICAL COMPOSITION FOR THE PREVENTION OR TREATMENT OF ALOPECIA COMPRISING *EREMOCHLOA OPHIUROIDES* EXTRACT OR FRACTIONS THEREOF AS AN ACTIVE INGREDIENT**

(71) Applicant: KOREA ATOMIC ENERGY RESEARCH INSTITUTE, Daejeon (KR)

(72) Inventors: Byung Yeoup Chung, Jeollabuk-do (KR); Hyoungwoo Bai, Jeollabuk-do (KR); Jae-Hyeon Cho, Gyeongsangnam-do (KR); Tae Hoon Kim, Daegu (KR)

(73) Assignee: Korea Atomic Energy Research Institute

( * ) Notice: Subject to any disclaimer, the term of this patent is extended or adjusted under 35 U.S.C. 154(b) by 300 days.

(21) Appl. No.: 16/712,060

(22) Filed: Dec. 12, 2019

(65) Prior Publication Data

US 2020/0113964 A1    Apr. 16, 2020

Related U.S. Application Data

(62) Division of application No. 16/338,331, filed as application No. PCT/KR2017/013923 on Nov. 30, 2017, now abandoned.

(30) Foreign Application Priority Data

Dec. 12, 2016 (KR) .................. 10-2016-0168960

(51) Int. Cl.
| | |
|---|---|
| *A61K 36/889* | (2006.01) |
| *A23L 33/105* | (2016.01) |
| *A61K 8/9789* | (2017.01) |
| *A61P 17/14* | (2006.01) |
| *A61Q 7/00* | (2006.01) |

(52) U.S. Cl.
CPC .......... *A61K 36/889* (2013.01); *A23L 33/105* (2016.08); *A61K 8/9789* (2017.08); *A61P 17/14* (2018.01); *A61Q 7/00* (2013.01)

(58) Field of Classification Search
None
See application file for complete search history.

(56) References Cited

U.S. PATENT DOCUMENTS

| | | | |
|---|---|---|---|
| 9,655,941 B2 | 5/2017 | Bai et al. | |
| 10,052,358 B2 | 8/2018 | Chung et al. | |
| 2007/0036742 A1 | 2/2007 | Roufs et al. | |
| 2015/0265667 A1* | 9/2015 | Bai ............... | A61K 36/899 424/750 |
| 2016/0263178 A1* | 9/2016 | Chung ............ | A61P 3/10 |
| 2019/0336560 A1 | 11/2019 | Chung et al. | |

FOREIGN PATENT DOCUMENTS

| | | |
|---|---|---|
| CN | 104812399 | 7/2015 |
| KR | 10-2011-0040363 | 4/2011 |
| KR | 10-2011-0054747 | 5/2011 |
| KR | 10-2012-0039384 | 4/2012 |
| KR | 10-1350826 | 1/2014 |
| KR | 10-2014-0015761 | 2/2014 |
| KR | 10-1400893 | 5/2014 |
| KR | 10-2016-0071523 | 6/2016 |
| KR | 10-2016-0105344 | 9/2016 |

OTHER PUBLICATIONS

Bai et al. "Drastic enhancement of maysin and maysin derivatives contents in the centipedegrass extracts by different stresses," IEEE Computer Society, 2012, 2012 International Conference on Biomedical Engineering and Biotechnology, pp. 187-189.
International Search Report and Written Opinion prepared by the Korean Intellectual Property Office dated Feb. 21, 2018, for International Application No. PCT/KR2017/013923.
Official Action with English Translation for Korea Patent Application No. 10-2017-0163088, dated Dec. 7, 2018, 6 pages.
Notice of Allowance with English Translation for Korea Patent Application No. 10-2017-0163088, dated Apr. 1, 2019, 7 pages.
Official Action for U.S. Appl. No. 16/338,331, dated Sep. 16, 2019 9 pages.
Extended Search Report for European Patent Application No. 17881157.6, dated Jun. 17, 2020, 6 pages.

* cited by examiner

*Primary Examiner* — Michael Barker
(74) *Attorney, Agent, or Firm* — Sheridan Ross P.C.

(57) ABSTRACT

The present invention relates to a composition comprising centipede grass extract as an active ingredient for the prevention or treatment of alopecia. Particularly, the centipede grass extract of the present invention increases the expression of hair growth related factors and accelerates hair growth, so that it can be effectively used for the prevention or treatment of alopecia.

2 Claims, 12 Drawing Sheets

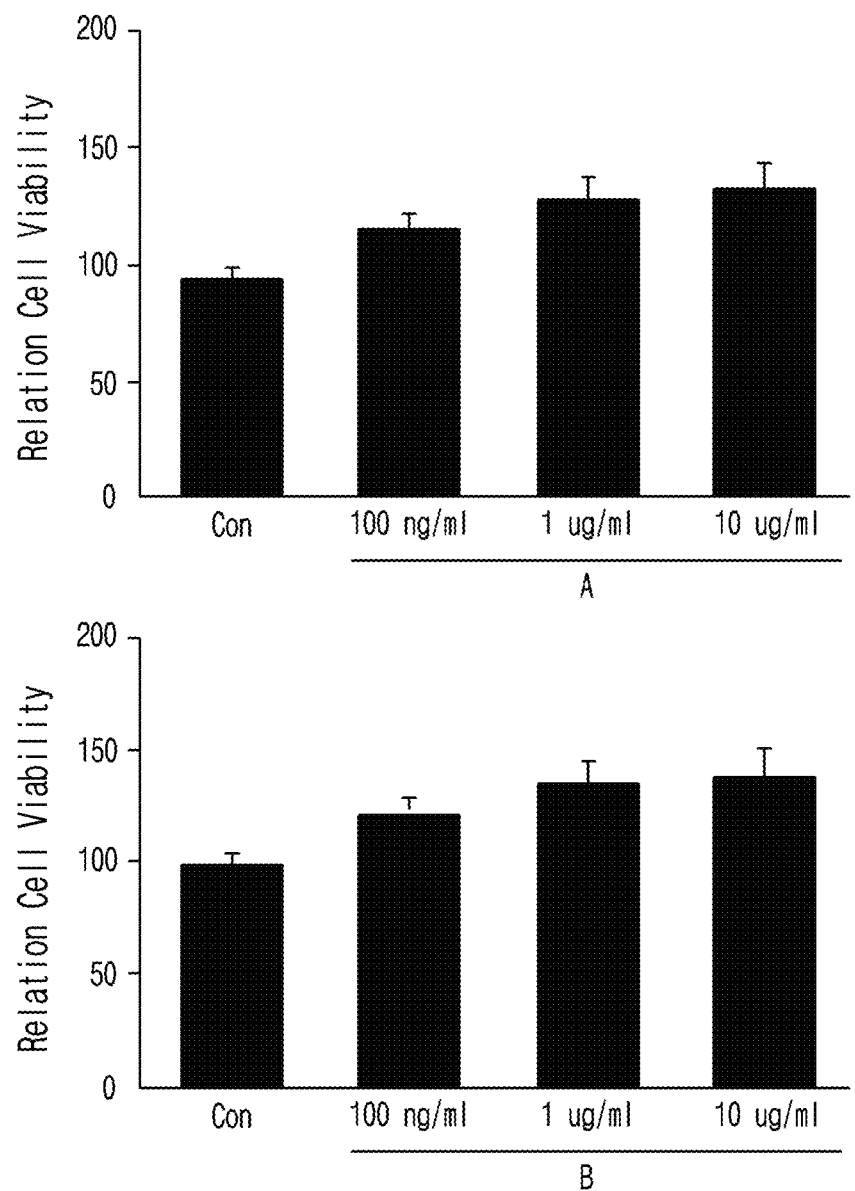
[Figure 1]

[Figure 2]
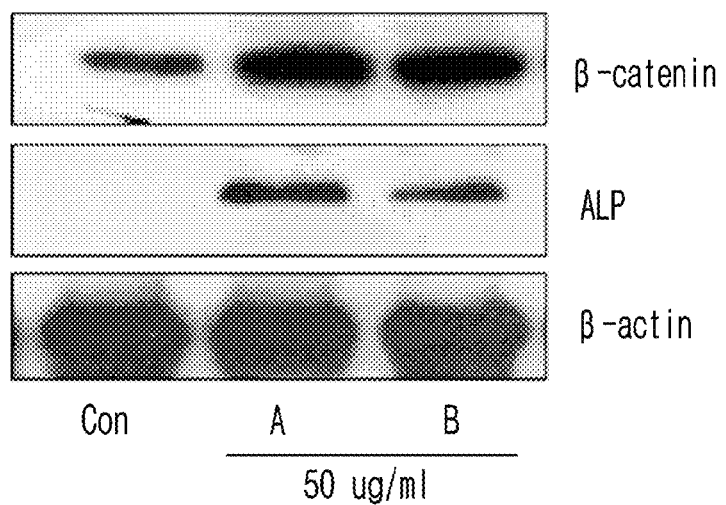

[Figure 3]
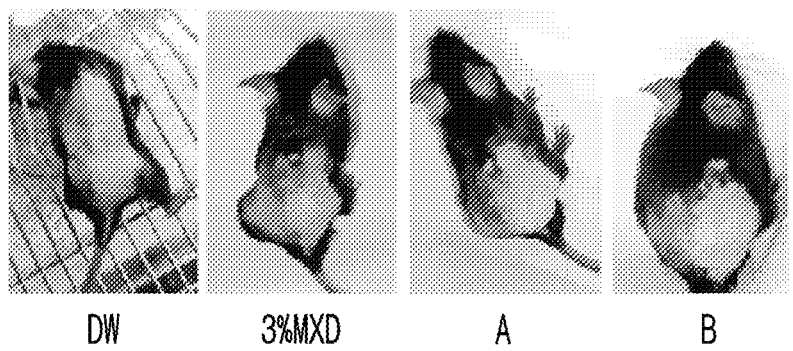

[Figure 4]
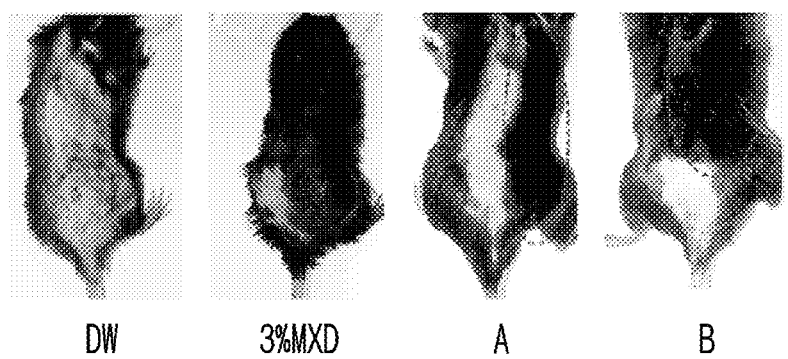

[Figure 5]
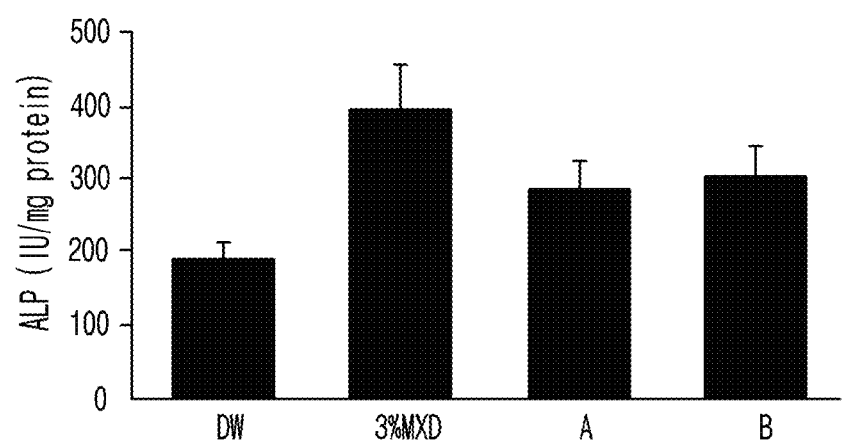

[Figure 6]
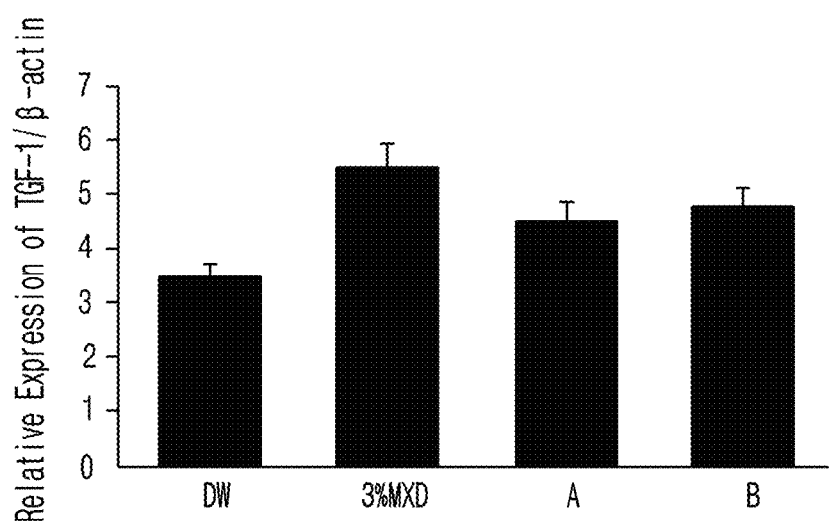

[Figure 7]
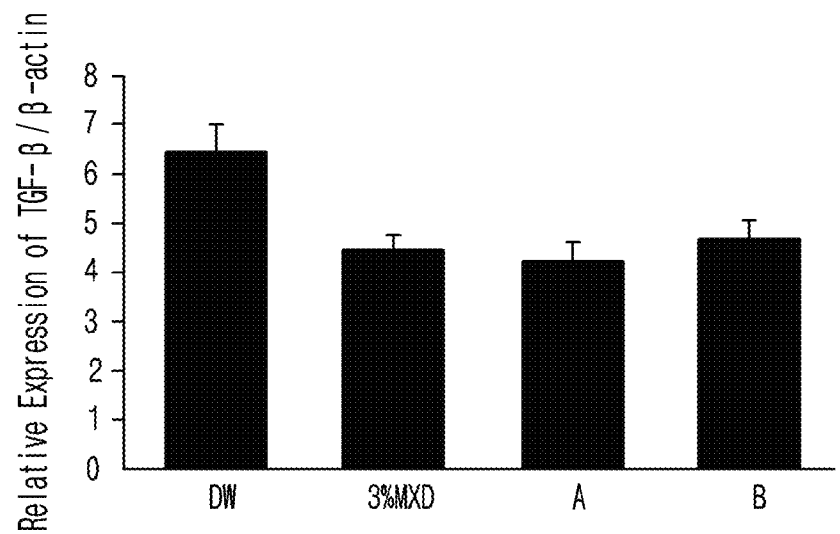

[Figure 8]
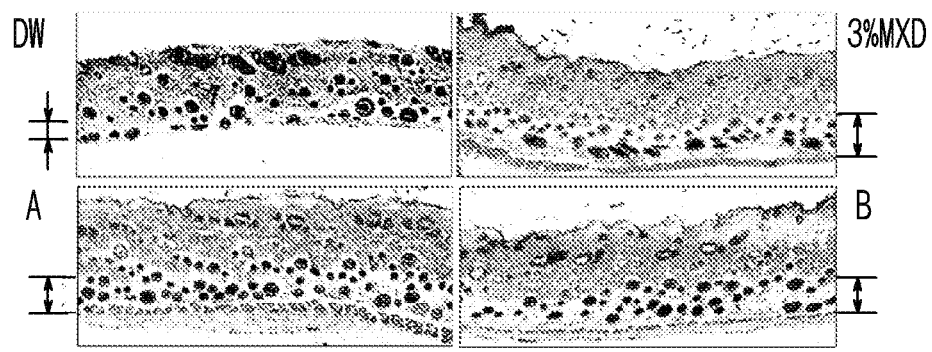

[Figure 9]
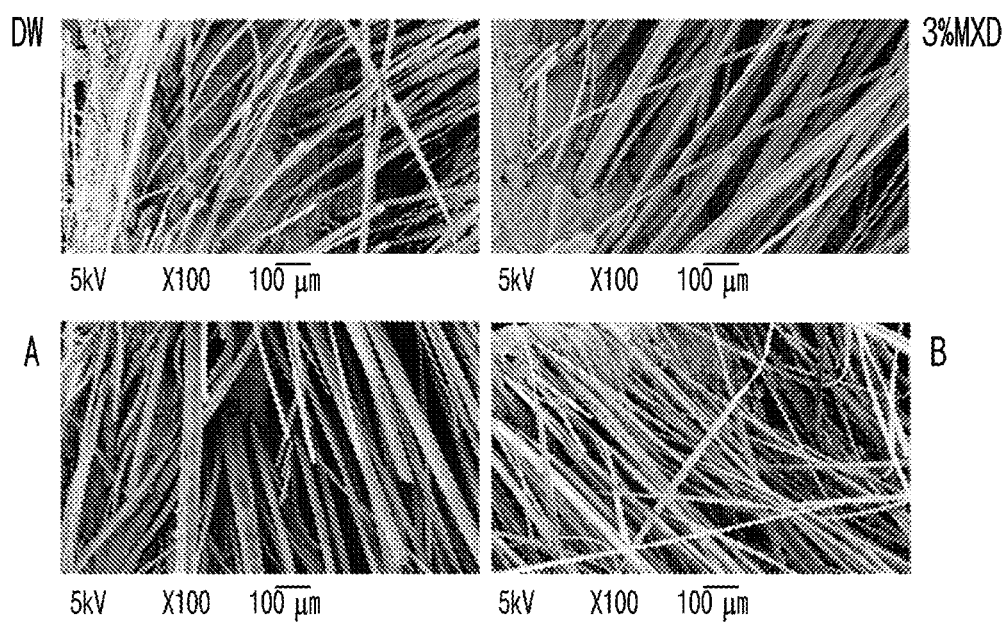

[Figure 10]
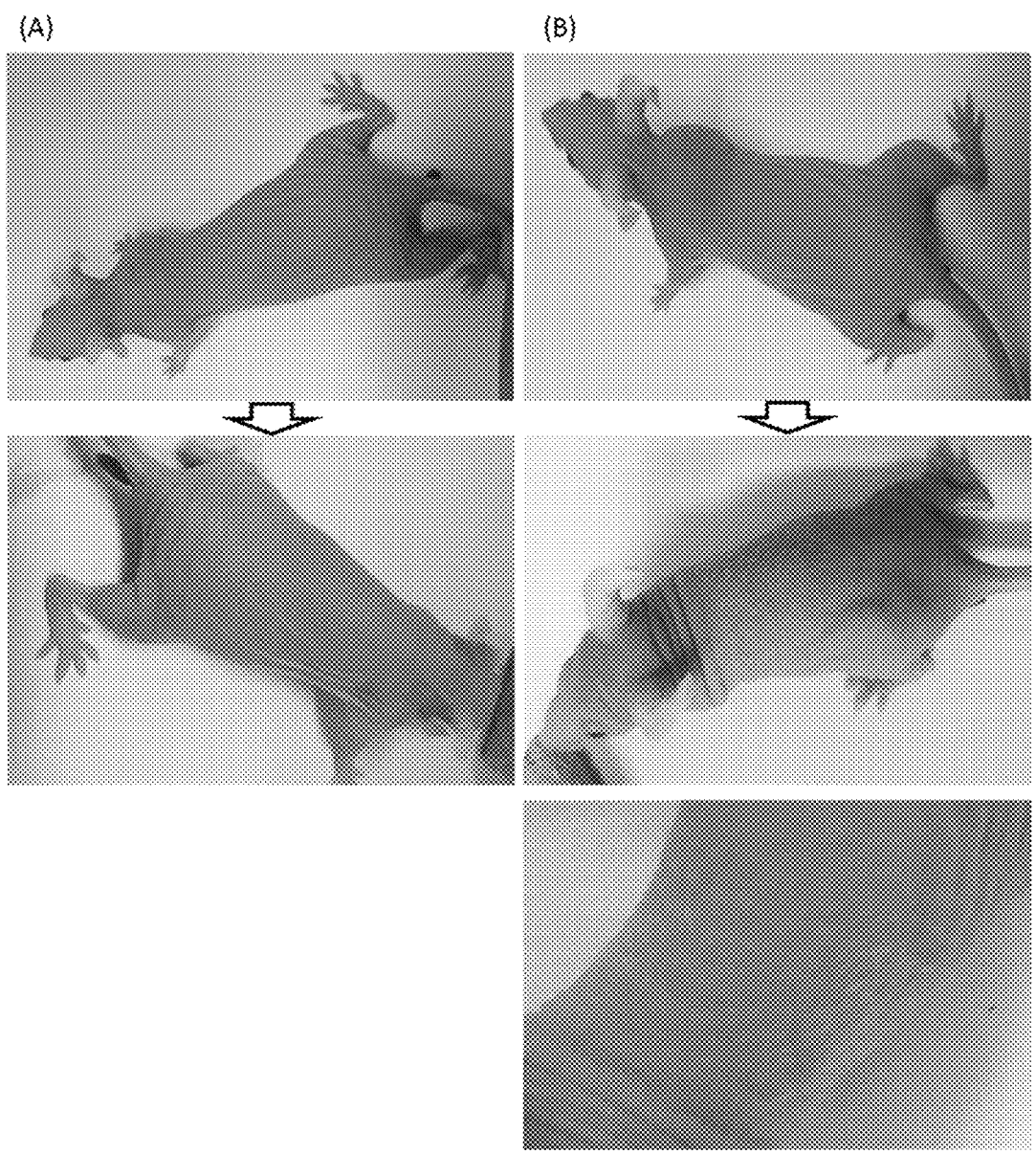

[Figure 11]
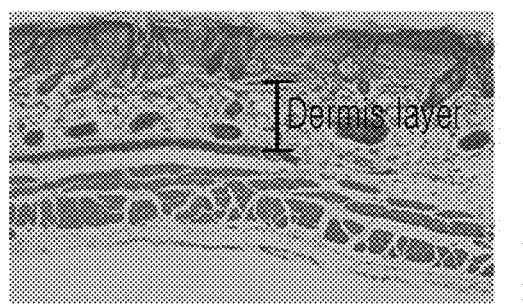 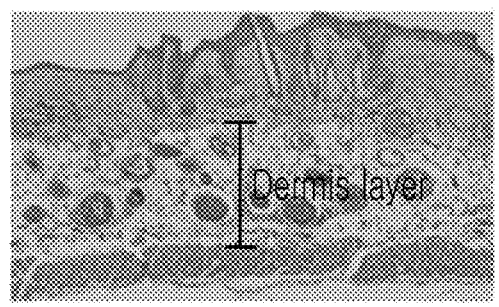
(a) (b)

[Figure 12]
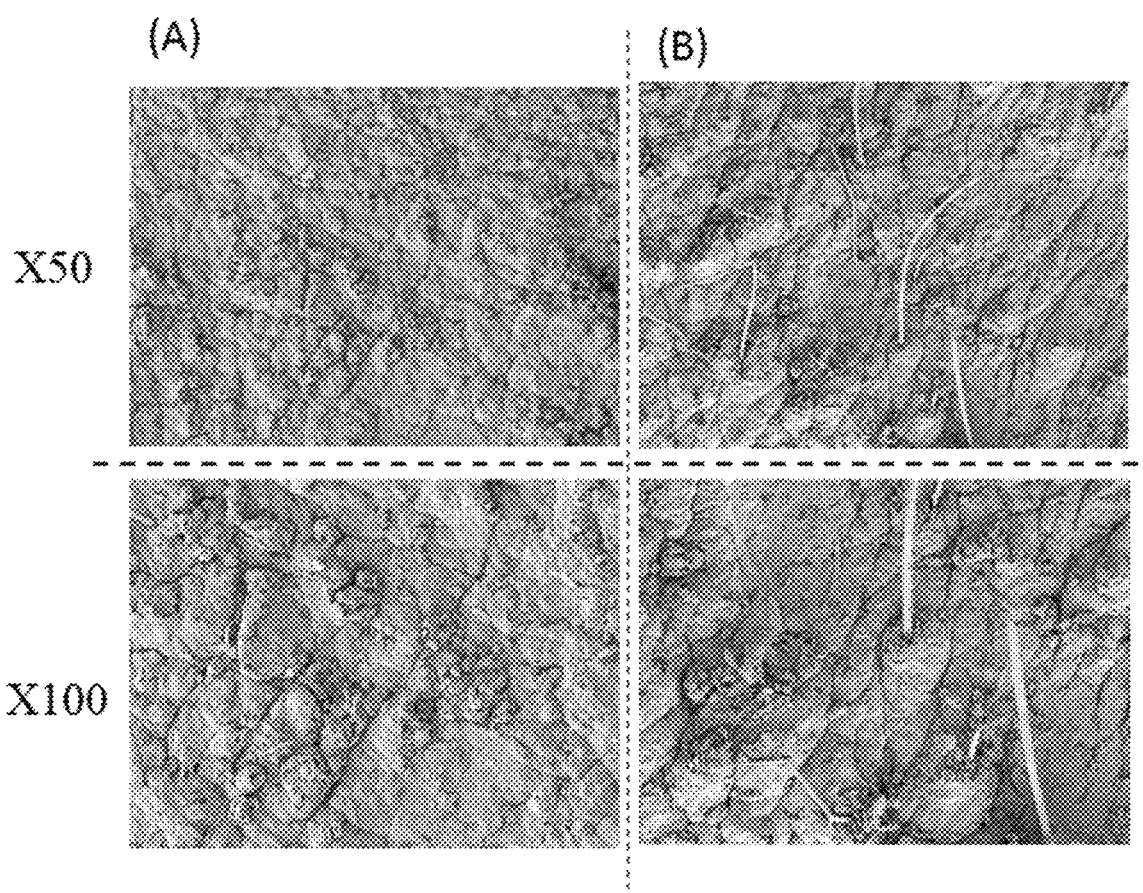

PHARMACEUTICAL COMPOSITION FOR THE PREVENTION OR TREATMENT OF ALOPECIA COMPRISING *EREMOCHLOA OPHIUROIDES* EXTRACT OR FRACTIONS THEREOF AS AN ACTIVE INGREDIENT

CROSS REFERENCE TO RELATED APPLICATIONS

This application is a divisional of U.S. patent application Ser. No. 16/338,331, filed Mar. 29, 2019, which is a national stage application under 35 U.S.C. 371 and claims the benefit of PCT Application No. PCT/KR2017/013923 having an international filing date of 30 Nov. 2017, which designated the United States, which PCT application claimed the benefit of the Republic of Korea Patent Application No. 10-2016-0168960 filed 12 Dec. 2016, the entire disclosures of each of which are incorporated herein by reference.

TECHNICAL FIELD

The present invention relates to a composition comprising a centipede grass (*Eremochloa ophiuroides*) extract or fractions thereof as an active ingredient for the prevention or treatment of alopecia.

The present invention also relates to a method for the prevention or treatment of alopecia containing the step of administering a pharmaceutically effective dose of the centipede grass extract or the fractions thereof to a subject.

The present invention also relates to a use of the pharmaceutical composition comprising the centipede grass extract or the fractions thereof as an active ingredient for the prevention, improvement, or the treatment of alopecia.

The preset invention also relates to a use of the composition for a health functional food or a hair growth composition comprising the centipede grass extract or the fractions thereof as an active ingredient for the prevention, improvement, or treatment of alopecia.

BACKGROUND ART

Alopecia indicates when there are no hairs where hairs normally grow. In general, when the dark and thick hairs are lost on the scalp, it is called alopecia. The reasons of alopecia are diverse. It has been known that genetic causes and androgen, the male hormone, are important factors in the development of baldness. Some of the female pattern alopecia is presumed to occur in the same pathway as the male pattern alopecia, but there are differences in clinical features.

Male pattern alopecia progresses from the age of 20s or 30s among those who have a family history with such a symptom as thinner hairs. At this time, the boundary between the forehead and hairs is pushed backward, and accordingly the forehead becomes wider with both temporal regions in the shape of the letter M, with which hair loss in the top of the head also progresses slowly. In the meantime, in the case of female pattern alopecia, the hair line upper the forehead remains but hairs in the center head become thinner and the volume shrinks. Female pattern alopecia is not so severe as male pattern alopecia and hardly becomes a complete bald with wide forehead.

The FDA approved and most representative drugs to accelerate hair growth are minoxidil and finasteride. However, long-term administration of minoxidil has side effects such as edema or arrhythmia and hairiness at unwanted areas. The effect of the drug is greatest at 6 months to 1 year after use, but then decreases gradually. Finasteride is a material that can inhibit the activity of 5-$\alpha$-reductase that is an enzyme involved in testosterone metabolism in hair follicles. This material, however, causes such side effects as sexual dysfunction, depression, and suicidal ideation. In addition, this material might increase the chance of birth defects. So, it is impossible to administer this material to women of childbearing age or pregnant women. Once the administration of these two drugs is stopped, alopecia progresses again. Valproic acid is another drug for the treatment of alopecia. However, it is taken during pregnancy; the cognitive development ability of child is significantly decreased. As such, all the drugs recently being used have side effects. Therefore, it is required to develop a safe alopecia treating agent with fewer side effects.

The inducers involved in the development of hair include $\beta$-catenin, ALP (alkaline phosphatase), and IGF-1 (insulin like growth factor-1). Particularly, $\beta$-catenin is a protein that determines the fate of stem cells in hair follicles. Stem cells differentiate into hair cells in the presence of $\beta$-catenin and into skin cells in the absence of $\beta$-catenin. ALP is involved in angiogenesis and provides nutrients to capillaries that are concentrated to induce dermis, thereby facilitating hair growth. IGF-1 induces transformation from the resting state of the hair, which is the main cause of alopecia, to the growing state. In the meantime, TGF-$\beta$ (transforming growth factor-$\beta$) is a hair growth inhibitory factor that attacks and destroys surrounding follicular cells, causing alopecia.

Centipede grass is warm-season turfgrass whose growth is late and creeping. This grass is perennial, which grows in a chunk of turf. Centipede grass belongs to Poaceae, and the scientific name thereof is *Eremochloa ophiuroides* (Munro) Hack. It is mainly distributed in China, East Asia, Indochina, Northeastern United States, Mesoamerica and Caribbean regions. It endures various kinds of soils but particularly prefers humid acidic soil and sandy soil with low fertility. The leaf is 15~30 mm in length and 2~4 mm in width and is flat with a white mid vein. It does not have hairs except collar part and the tip of leaf is round. The stem has a compressed sheath and the roots are stolons having thin branches. The flower of it has a raceme in 3~5 inches. This raceme is purple and slightly flat-shaped and has two rows of spikelets.

Centipede grass is mainly used as lawn or turf grass and is used as forage for its high leaf rate and good taste. Korean Patent No. 10-1350826 describes a use of a centipede grass extract or a fraction thereof as a composition for the prevention and treatment of diabetes. Korean Patent No. 10-1398546 describes a use of a centipede grass extract or a fraction thereof as a composition for the improvement of skin disease.

Thus, the present inventors tried to develop a non-toxic, safe therapeutic agent for alopecia. In the course of our study, the present inventors confirmed that the centipede grass extract could increase the expression of hair growth-related factors and promote hair growth in a mouse model, leading to the completion of the present invention.

DISCLOSURE

Technical Problem

It is an object of the present invention to provide a pharmaceutical composition for the prevention or treatment of alopecia which comprises a centipede grass extract or a fraction thereof as an active ingredient.

It is another object of the present invention to provide a health functional food for the improvement of alopecia which comprises a centipede grass extract or a fraction thereof as an active ingredient.

It is also an object of the present invention to provide a hair growth composition which comprises a centipede grass extract or a fraction thereof as an active ingredient.

Technical Solution

To achieve the above objects, the present invention provides a pharmaceutical composition for the prevention or treatment of alopecia which comprises a centipede grass extract as an active ingredient.

The present invention also provides a health functional food for the improvement of alopecia which comprises a centipede grass extract as an active ingredient.

The present invention also provides a hair growth composition which comprises a centipede grass extract as an active ingredient.

The present invention also provides a pharmaceutical composition for the prevention or treatment of alopecia which comprises a fraction of the centipede grass extract prepared by additional extraction of the extract using an organic solvent as an active ingredient.

The present invention also provides a health functional food for the improvement of alopecia which comprises a fraction of the centipede grass extract prepared by additional extraction of the extract using an organic solvent as an active ingredient.

The present invention also provides a hair growth composition which comprises a fraction of the centipede grass extract prepared by additional extraction of the extract using an organic solvent as an active ingredient.

The present invention also provides a method for preventing or treating alopecia containing the step of administering a pharmaceutically effective dose of a centipede grass extract to a subject.

The present invention also provides a method for preventing or treating alopecia containing the step of administering a pharmaceutically effective dose of a fraction of the centipede grass extract prepared by additional extraction of the centipede grass extract using an organic solvent to a subject.

The present invention also provides a use of the pharmaceutical composition comprising a centipede grass extract as an active ingredient for the prevention or treatment of alopecia.

The present invention also provides a use of the health functional food comprising a centipede grass extract as an active ingredient for the prevention or improvement of alopecia.

The present invention also provides a use of the hair growth composition comprising a centipede grass extract as an active ingredient for the prevention or treatment of alopecia.

The present invention also provides a use of the pharmaceutical composition comprising a fraction of the centipede grass extract prepared by additional extraction of the centipede grass extract using an organic solvent as an active ingredient for the prevention or treatment of alopecia.

The present invention also provides a use of the health functional food comprising a fraction of the centipede grass extract prepared by additional extraction of the centipede grass extract using an organic solvent as an active ingredient for the prevention or improvement of alopecia.

In addition, the present invention provides a use of the hair growth composition comprising a fraction of the centipede grass extract prepared by additional extraction of the centipede grass extract using an organic solvent as an active ingredient for the prevention or improvement of alopecia.

Advantageous Effects

The centipede grass extract or the fraction thereof of the present invention increases the expression of hair growth-related factors and promotes hair growth thereby, so that it can be effectively used for the prevention or treatment of alopecia.

DESCRIPTION OF DRAWINGS

The application of the preferred embodiments of the present invention is best understood with reference to the accompanying drawings, wherein:

FIG. 1 is a graph illustrating the skin cell proliferative activity of the ethyl acetate fraction (A) or the butanol fraction (B) of the centipede grass extract.

FIG. 2 is a diagram illustrating the expression pattern of β-catenin and ALP according to the ethyl acetate fraction (A) or the butanol fraction (B) of the centipede grass extract.

FIG. 3 is a photograph taken after distributing the ethyl acetate fraction (A) or the butanol fraction (B) of the centipede grass extract on the hair-removed mouse skin.

FIG. 4 is a photograph illustrating the hair growth effect on the hair-removed mouse skin after the distribution of the ethyl acetate fraction (A) or the butanol fraction (B) of the centipede grass extract.

FIG. 5 is a graph illustrating the changes of the ALP enzyme activity in the mouse skin tissue according to the ethyl acetate fraction (A) or the butanol fraction (B) of the centipede grass extract.

FIG. 6 is a graph illustrating the expression of IGF-1 mRNA induced by the ethyl acetate fraction (A) or the butanol fraction (B) of the centipede grass extract in the mouse skin tissue.

FIG. 7 is a graph illustrating the expression of TGF-β mRNA induced by the ethyl acetate fraction (A) or the butanol fraction (B) of the centipede grass extract in the mouse skin tissue.

FIG. 8 is a photograph illustrating the growth of hair follicles in the mouse skin tissue distributed with the ethyl acetate fraction (A) or the butanol fraction (B) of the centipede grass extract, observed after staining.

FIG. 9 is a photograph of fluorescence microscope illustrating hair growth on the mouse skin after the distribution of the ethyl acetate fraction (A) or the butanol fraction (B) of the centipede grass extract thereon.

FIG. 10 is a photograph illustrating the hair growth effect on the skin of nude mouse after the distribution of the centipede grass extract (B).

FIG. 11 is a photograph illustrating the growth of hair follicles on the skin of nude mouse after the distribution of the centipede grass extract (B), observed after staining.

FIG. 12 is a photograph of fluorescence microscope illustrating hair growth on the skin of nude mouse after the distribution of the centipede grass extract (B) thereon.

BEST MODE

Hereinafter, the present invention is described in detail.

The present invention provides a pharmaceutical composition for the prevention or treatment of alopecia which comprises a centipede grass extract as an active ingredient.

The present invention also provides a method for preventing or treating alopecia containing the step of administering a pharmaceutically effective dose of a centipede grass extract to a subject.

The present invention also provides a use of the pharmaceutical composition comprising a centipede grass extract as an active ingredient for the prevention or treatment of alopecia.

The centipede grass above is either purchased or cultivated. All the leaves, stems or roots of the centipede grass can be used. In an embodiment of the present invention, centipede grass leaves were used.

The extract can be extracted by using water, alcohol, or the mixture thereof as a solvent. The said alcohol is preferably $C_1$~$C_4$ lower alcohol. The lower alcohol herein is preferably ethanol or methanol. In an embodiment of the present invention, the alcohol was 80% methanol.

The extraction method can be any conventional method known to those in the art, which is exemplified by extraction under reduced pressure, boiling water extraction, filtration, hot water extraction, immersion extraction, reflux extraction, cold extraction, steam extraction, room temperature extraction or ultrasonic extraction. In an embodiment of the present invention, the extraction method was room temperature extraction.

The extraction solvent is added to the dried centipede grass at the volume of 20~50 times the total volume of the centipede grass, preferably 25~40 times, and more preferably 30~35 times. In an embodiment of the present invention, the extraction solvent was added to the dried centipede grass at the volume of 32 times the total volume of the centipede grass.

The extraction can be performed at 10~50° C., preferably at 10~40° C., and more preferably at 10~30° C. In an embodiment of the present invention, the extraction was performed at 15~25° C. The extraction can be performed for 2~5 days, and preferably for 2~4 days. In an embodiment of the present invention, the extraction was performed for 3 days. The extraction can be repeated 1~5 times, and preferably 2~4 times. In an embodiment of the present invention, the extraction was repeated 3 times.

In a preferred embodiment of the present invention, methanol was added to the centipede grass leaf sample to obtain a centipede grass extract. Then, an ethyl acetate fraction and a butanol fraction were obtained from the centipede grass extract. The present inventors confirmed that the fractions above could increase the expressions of β-catenin and ALP in skin cells and could increase the activity of ALP enzyme and the expression of IGF-1 in the mouse skin tissues, but reduce the expression of TGF-β, and accordingly demonstrate hair growth inducing effect (see FIGS. 1~12). Therefore, it was confirmed that the centipede grass extract including the fraction thereof can be effectively used for the treatment of alopecia.

The pharmaceutical composition preferably includes the centipede grass extract of the present invention by 10~95 weight % for the total weight of the composition as an active ingredient. The pharmaceutical composition of the present invention can include, in addition to the active ingredient, one or more effective ingredients having the same or similar function to the active ingredient.

The pharmaceutical composition of the present invention can include any generally used carrier, diluent, excipient, or a combination of at least two of those. The pharmaceutically acceptable carrier can be any carrier that is able to deliver the composition of the present invention in human body without limitation, which is exemplified by the compounds described in Merck Index, 13$^{th}$ ed., Merck & Co. Inc., such as saline, sterilized water, Ringer's solution, buffered saline, dextrose solution, maltodextrin solution, glycerol, ethanol, liposome and a mixture comprising one or more of those components. If necessary, a general additive such as antioxidant, buffer, and bacteriostatic agent can be additionally added.

The composition of the present invention can be prepared by mixing with generally used diluents or excipients such as fillers, extenders, binders, wetting agents, disintegrating agents and surfactant.

The composition of the present invention can be administered orally or parenterally and be used in general forms of pharmaceutical formulation. Solid formulations for oral administration are tablets, pills, powders, granules, capsules, and troches. These solid formulations are prepared by mixing one or more suitable excipients such as starch, calcium carbonate, sucrose or lactose, gelatin, etc. Except for the simple excipients, lubricants, for example magnesium stearate, talc, etc., can be used. Liquid formulations for oral administrations are suspensions, solutions, emulsions and syrups, and the above-mentioned formulations can contain various excipients such as wetting agents, sweeteners, aromatics and preservatives.

Formulations for parenteral administration are sterilized aqueous solutions, water-insoluble excipients, suspensions, emulsions, lyophilized preparations, and injections.

Water insoluble excipients and suspensions can contain, in addition to the active compound or compounds, propylene glycol, polyethylene glycol, vegetable oil like olive oil, injectable ester like ethylolate, etc.

The composition of the present invention can be administered orally or parenterally, and the parenteral administration herein is exemplified by external skin application, intraperitoneal injection, intrarectal injection, subcutaneous injection, intravenous injection, intramuscular injection, or intrathoracic injection.

The composition of the present invention is administered in a pharmaceutically effective dose. The pharmaceutically effective dose can be adjusted according to disease type, severity of disease, drug activity, sensitiveness to drug, administration time, administration pathway, excretion, treatment period, and other drugs co-treated, etc. The composition of the present invention can be administered alone or in combination with other therapeutic agents. When the composition of the present invention is co-administered with other therapeutic agents, the administration can be sequential or simultaneous.

For the desired effect, the amount of the active ingredient contained in the pharmaceutical composition of the present invention can be 0.001~10,000 mg/kg, and preferably 0.1~5 g/kg. The pharmaceutical composition of the present invention may be administered once a day or with divided doses several times a day.

The present invention also provides a health functional food for the improvement of alopecia which comprises a centipede grass extract as an active ingredient. The present invention also provides a use of the health functional food comprising a centipede grass extract as an active ingredient for the prevention or improvement of alopecia.

The extract can have the characteristics as described above. For example, the centipede grass above is either purchased or cultivated. All the leaves, stems or roots of the centipede grass can be used. In an embodiment of the present invention, centipede grass leaves were used.

The extract can be extracted by using water, alcohol, or the mixture thereof as a solvent. The said alcohol is preferably $C_1$~$C_4$ lower alcohol. The lower alcohol herein is preferably ethanol or methanol. In an embodiment of the present invention, the alcohol was 80% methanol.

In a preferred embodiment of the present invention, methanol was added to the centipede grass leaf sample to obtain a centipede grass extract. Then, an ethyl acetate fraction and a butanol fraction were obtained from the centipede grass extract. The present inventors confirmed that the fractions above could increase the expressions of β-catenin and ALP in skin cells and could increase the activity of ALP enzyme and the expression of IGF-1 in the mouse skin tissues, but reduce the expression of TGF-β, and accordingly demonstrate hair growth inducing effect (see FIGS. 1~12). Therefore, it was confirmed that the centipede grass extract including the fraction thereof can be effectively used for the improvement of alopecia.

The content of the centipede grass extract, which is an active ingredient added to the health functional food, can be determined depending on the purpose. Generally, the health functional food preferably includes the centipede grass extract by 0.01~90 weight part for the total weight of the health functional food.

In addition, there is no particular limitation on the form and the kind of the health functional food. The form of the health functional food to which the extract of the present invention is added can be tablets, capsules, powders, granules, solutions or pills.

The health functional food of the present invention can additionally include various flavors or natural carbohydrates, etc., like other health foods. The natural carbohydrates above can be one of monosaccharides such as glucose and fructose, disaccharides such as maltose and sucrose, polysaccharides such as dextrin and cyclodextrin, and glucose alcohols such as xilytole, sorbitol and erythritol. Besides, natural sweetening agents such as thaumatin and stevia extract, and synthetic sweetening agents such as saccharin and aspartame can be included as a sweetening agent.

In addition to the ingredients mentioned above, the health functional food of the present invention can include in variety of nutrients, vitamins, minerals, flavors, coloring agents, pectic acid and its salts, alginic acid and its salts, organic acid, protective colloidal viscosifiers, pH regulators, stabilizers, antiseptics, glycerin, or alcohols. All the mentioned ingredients can be added singly or together. The mixing ratio of those ingredients does not matter in fact, but in general, each can be added by 0.01~0.1 weight part per 100 weight part of the extract of the present invention.

The present invention also provides a hair growth composition which comprises a centipede grass extract as an active ingredient.

The present invention also provides a use of the hair growth composition comprising a centipede grass extract as an active ingredient for the prevention or treatment of alopecia.

The extract can have the characteristics as described above. For example, the centipede grass above is either purchased or cultivated. All the leaves, stems or roots of the centipede grass can be used. In an embodiment of the present invention, centipede grass leaves were used.

The extract can be extracted by using water, alcohol, or the mixture thereof as a solvent. The said alcohol is preferably $C_1$~$C_4$ lower alcohol. The lower alcohol herein is preferably ethanol or methanol. In an embodiment of the present invention, the alcohol was 80% methanol.

In a preferred embodiment of the present invention, methanol was added to the centipede grass leaf sample to obtain a centipede grass extract. Then, an ethyl acetate fraction and a butanol fraction were obtained from the centipede grass extract. The present inventors confirmed that the fractions above could increase the expressions of β-catenin and ALP in skin cells and could increase the activity of ALP enzyme and the expression of IGF-1 in the mouse skin tissues, but reduce the expression of TGF-β, and accordingly demonstrate hair growth inducing effect (see FIGS. 1~12). Therefore, it was confirmed that the centipede grass extract including the fraction thereof can be effectively used as a hair growth composition.

The hair growth composition of the present invention can contain the centipede grass extract at the concentration of 0.001~99.99 weight %, and preferably 0.1~50 weight % by the total weight of the composition. However, the ratio above can be adjusted according to the purpose of use or the severity of alopecia as long as it does not cause toxicity to the human body.

The hair growth composition of the present invention can include general cosmetic materials or drug materials in addition to the centipede grass extract at a proper concentration. For example, purified water, mineral water, ethanol, glycerin, squalene, 1,3-propylene glycol, 1,3-butylene glycol, castor oil, tsubaki oil, liquid petrolatum, surfactants, emulsifiers, thickeners, antiseptics, anti-oxidants, fragrances, or carriers can be included.

The composition of the present invention can include, in addition to the components mentioned above, a component to deliver nutritions to hair follicles and another supplementary component to promote hair growth, which are exemplified by vitamins such as vitamin A, vitamin B1, vitamin B2, niacin (nicotinic acid), vitamin C, vitamin E, sodium pantothenate, potassium pantothenate, or biotin H (vitamin H); amino acid such as dopa; and animal/vegetable oils such as hempseed oil, egg oil, olive oil, camellia oil, rapeseed oil, sesame oil, and germ oil. The preferable concentration of such a supplementary material is 0.0001~10 weight % by the total volume of the composition, and more preferably is 0.01~1 weight %.

The composition of the present invention can be directly applied or dispersed on hair or scalp. So, the composition can be prepared in the form of hair tonic, hair lotion, hair cream, hair spray, hair mousse, hair gel, hair conditioner, hair shampoo, hair rinse, hair pack, hair treatment, eyebrow hair growth agent, eyelash hair growth agent or eyelash nutrient, pet shampoo or pet rinse.

The composition of the present invention can be formulated in any form that can be conventionally prepared in this field, which is exemplified by cream, lotion, tonic, spray, aerosol, oil, solution, suspension, gel, ointment, emulsion, or paste.

In the case that the composition of the present invention is formulated as paste, cream or gel, the proper carrier can be selected from the group consisting of animal oil, vegetable oil, wax, paraffin, starch, tracanth, cellulose derivative, polyethylene glycol, silicon, bentonite, silica, talk and zinc oxide.

In the case that the composition of the present invention is formulated as spray, the proper carrier can be selected from the group consisting of lactose, talc, silica, aluminum hydroxide, calcium silicate and polyamide powder, and in particular a propellant such as chlorofluorohydrocarbon, propane/butane or dimethyl ether can be additionally included.

In the case that the composition of the present invention is formulated as liquid, the proper carrier can be selected from the group consisting of solvent, solubilizer and emulsifier, which is exemplified by water, ethanol, isopropanol, ethyl carbonate, ethyl acetate, benzyl alcohol, benzyl benzoate, propylene glycol, 1,3-butyl glycol oil, glycerol aliphatic ester, polyethylene glycol and fatty acid ester of sorbitan.

In the case that the composition of the present invention is formulated as suspension, the proper carrier can be selected from the group consisting of liquid diluent such as water, ethanol or propylene glycol; suspending agent such as ethoxylated isostearyl alcohol, polyoxyethylene sorbitol ester and polyoxyethylene sorbitan ester; microcrystalline cellulose; aluminum methahydroxide; bentonite; agar; and tragacanth.

The present invention also provides a pharmaceutical composition for the prevention or treatment of alopecia which comprises a fraction of the centipede grass extract prepared by additional extraction of the extract using an organic solvent as an active ingredient.

The present invention also provides a method for preventing or treating alopecia containing the step of administering a pharmaceutically effective dose of a fraction of the centipede grass extract prepared by additional extraction of the centipede grass extract using an organic solvent to a subject.

The present invention also provides a use of the pharmaceutical composition comprising a fraction of the centipede grass extract prepared by additional extraction of the centipede grass extract using an organic solvent as an active ingredient for the prevention or treatment of alopecia.

The extract can have the characteristics as described above. For example, the centipede grass above is either purchased or cultivated. All the leaves, stems or roots of the centipede grass can be used. In an embodiment of the present invention, centipede grass leaves were used.

The extract can be extracted by using water, alcohol, or the mixture thereof as a solvent. The said alcohol is preferably $C_1$~$C_4$ lower alcohol. The lower alcohol herein is preferably ethanol or methanol. In an embodiment of the present invention, the alcohol was 80% methanol.

The organic solvent herein can be n-hexane, ethyl acetate or butanol, particularly ethyl acetate or butanol.

The fraction can have the characteristics as described above. For example, the fraction can be an ethyl acetate fraction or a butanol fraction. The ethyl acetate fraction can be obtained by extracting the centipede grass methanol extract with n-hexane, removing the soluble layer, and extracting the remaining water layer with ethyl acetate. The butanol fraction can be obtained by extracting the ethyl acetate fraction of centipede grass with butanol.

In a preferred embodiment of the present invention, methanol was added to the centipede grass leaf sample to obtain a centipede grass extract. Then, an ethyl acetate fraction and a butanol fraction were obtained from the centipede grass extract. The present inventors confirmed that the fractions above could increase the expressions of β-catenin and ALP in skin cells and could increase the activity of ALP enzyme and the expression of IGF-1 in the mouse skin tissues, but reduce the expression of TGF-β, and accordingly demonstrate hair growth inducing effect (see FIGS. 1~12).

The present invention also provides a health functional food for the improvement of alopecia which comprises a fraction of the centipede grass extract prepared by additional extraction of the extract using an organic solvent as an active ingredient.

The present invention also provides a use of the health functional food comprising a fraction of the centipede grass extract prepared by additional extraction of the centipede grass extract using an organic solvent as an active ingredient for the prevention or improvement of alopecia.

The extract can have the characteristics as described above. For example, the centipede grass above is either purchased or cultivated. All the leaves, stems or roots of the centipede grass can be used. In an embodiment of the present invention, centipede grass leaves were used.

The extract can be extracted by using water, alcohol, or the mixture thereof as a solvent. The said alcohol is preferably $C_1$~$C_4$ lower alcohol. The lower alcohol herein is preferably ethanol or methanol. In an embodiment of the present invention, the alcohol was 80% methanol.

The organic solvent herein can be n-hexane, ethyl acetate or butanol, particularly ethyl acetate or butanol.

The fraction can have the characteristics as described above. For example, the fraction can be an ethyl acetate fraction or a butanol fraction. The ethyl acetate fraction can be obtained by extracting the centipede grass methanol extract with n-hexane, removing the soluble layer, and extracting the remaining water layer with ethyl acetate. The butanol fraction can be obtained by extracting the ethyl acetate fraction of centipede grass with butanol.

The health functional food can have the characteristics as described above.

In a preferred embodiment of the present invention, methanol was added to the centipede grass leaf sample to obtain a centipede grass extract. Then, an ethyl acetate fraction and a butanol fraction were obtained from the centipede grass extract. The present inventors confirmed that the fractions above could increase the expressions of β-catenin and ALP in skin cells and could increase the activity of ALP enzyme and the expression of IGF-1 in the mouse skin tissues, but reduce the expression of TGF-β, and accordingly demonstrate hair growth inducing effect (see FIGS. 1~12).

The present invention also provides a hair growth composition which comprises a fraction of the centipede grass extract prepared by additional extraction of the extract using an organic solvent as an active ingredient.

In addition, the present invention provides a use of the hair growth composition comprising a fraction of the centipede grass extract prepared by additional extraction of the centipede grass extract using an organic solvent as an active ingredient for the prevention or improvement of alopecia.

The extract can have the characteristics as described above. For example, the centipede grass above is either purchased or cultivated. All the leaves, stems or roots of the centipede grass can be used. In an embodiment of the present invention, centipede grass leaves were used.

The extract can be extracted by using water, alcohol, or the mixture thereof as a solvent. The said alcohol is preferably $C_1$~$C_4$ lower alcohol. The lower alcohol herein is preferably ethanol or methanol. In an embodiment of the present invention, the alcohol was 80% methanol.

The organic solvent herein can be n-hexane, ethyl acetate or butanol, particularly ethyl acetate or butanol.

The fraction can have the characteristics as described above. For example, the fraction can be an ethyl acetate fraction or a butanol fraction. The ethyl acetate fraction can be obtained by extracting the centipede grass methanol extract with n-hexane, removing the soluble layer, and extracting the remaining water layer with ethyl acetate. The butanol fraction can be obtained by extracting the ethyl acetate fraction of centipede grass with butanol.

The hair growth composition can have the characteristics as described above.

In a preferred embodiment of the present invention, methanol was added to the centipede grass leaf sample to obtain a centipede grass extract. Then, an ethyl acetate fraction and a butanol fraction were obtained from the centipede grass extract. The present inventors confirmed that the fractions above could increase the expressions of β-catenin and ALP in skin cells and could increase the activity of ALP enzyme and the expression of IGF-1 in the mouse skin tissues, but reduce the expression of TGF-β, and accordingly demonstrate hair growth inducing effect (see FIGS. 1~12).

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Preparation of Centipede Grass Extract

The centipede grass seeds were purchased from Fukukaen Nursery and Blub Co. Ltd, Japan, which grew in the field at Advanced Radiation Technology Institute, Korea Atomic Energy Research Institute, Jeongeup, Korea. Leaves were collected from the grown centipede grass. The obtained leaves were stored at −80° C. 7 kg of the centipede grass leaves were mixed with 225 $l$ of 80% methanol was added thereto 3 times, and the mixture was grinded in a mixer. Precipitation was induced at room temperature for 3 days. The obtained extract was concentrated under reduced pressure at 50° C. As a result, 502.5 g of a centipede grass methanol extract was prepared.

Example 2: Preparation of Centipede Grass Fraction

The centipede grass methanol extract obtained in Example 1 was fractionated using organic solvents according to the polarity. The methanol extract concentrated under reduced pressure was suspended in 3 $l$ of water added with 10% methanol. First, 3 $l$ of hexane (N-hexane), the low-polar solvent was added thereto 5 times. The fraction was concentrated under reduced pressure and dried. As a result, 44.0311 g of a hexane fraction was obtained. Then, 3 $l$ of ethyl acetate was added to the water layer 5 times, followed by fractionation. The fraction was concentrated under reduced pressure and dried. As a result, 28.1328 g of an ethyl acetate fraction was obtained. Then, 3 $l$ of butanol was added to the water layer 5 times, followed by fractionation. The fraction was concentrated under reduced pressure and dried. As a result, 111.1267 g of a butanol fraction and 213.371 g of a water-soluble fraction were obtained.

Experimental Example 1: Confirmation of Skin Cell Proliferation Activity

The effect of the ethyl acetate and butanol fractions of the centipede grass extract on the skin cell (HaCaT) proliferation was investigated by MTT assay.

Particularly, HaCaT cells were diluted in the medium supplemented with 10% FBS, which was distributed in a 24 well plate at the density of 50,000 cells/well, followed by culture for 24 hours. Upon completion of the culture, the medium was replaced with the medium supplemented with 1% FBS to minimize the effect of other ingredients included in the serum, followed by culture for 24 hours. Thereafter, the medium was added or not added with the centipede grass fraction at the concentration of 100 ng/m$l$, 1 μg/ml, or 10 μg/ml, and the cells were further cultured. The medium of the cultured cells was replaced with the medium supplemented with 0.5 mg/ml of MTT [3-(4,5-dimethylthiazol-2-yl)-2,5-diphenyltetrazolium bromide] (Amresco, USA), followed by culture at 37° C. 3 hours later, MTT reagent was clearly washed out with PBS and 200 me of DMSO (dimethyl sulfoxide, Amresco) was added thereto to dissolve formazan completely. The dissolved formazan was transferred into a 96 well plate. $OD_{540}$ was measured by using Infinite M200 (TECAN, Switzerland).

As a result, as shown in FIG. 1, the cell proliferation activity was increased in the group treated with the centipede grass ethyl acetate fraction (A) or butanol fraction (B), compared with the control (Con) treated with distilled water (FIG. 1).

Experimental Example 2: Confirmation of Hair Growth Inducing Factor Expression

Western blotting was performed to confirm the effect of the centipede grass ethyl acetate and butanol fractions on the expressions of the hair growth inducing factors 1-catenin and ALP.

Particularly, HaCaT cells were distributed in 60 mm dishes at the density of $2 \times 10^6$ cells (3 m$l$)/dish, followed by culture in a 37° C., 5% $CO_2$ incubator for 12 hours to attach the cells on the dish. The cells were treated with the centipede grass ethyl acetate fraction or butanol fraction at the concentration of 50 μg/m$l$. The cells were collected and suspended in a lysis buffer (150 mM NaCl, 10 mM Tris-HCl, 1 mM EGTA, 1 mM EDTA, 0.2 mM sodium vanadate, 0.5% Nonidet P-40) containing a protease inhibitor (1 mM PMSF, 0.1 mM okadaic acid, aprotinin, leupeptin, and pepstatin). The mixture was left on ice for 30 minutes and then sonicated. The cell lysate was diluted in 2×SDS stop buffer (2% SDS, 5 mM EGTA, 5 mM EDTA, 25 mM dithiothreitol, 10% glycerol, 0.01% bromophenol blue, 0.25 M Tris-Cl (pH 6.8)), followed by boiling at 100° C. for 5 minutes. The equal amount of protein was separated from each cell lysate by 10% SDS-PAGE, and the separated protein was transferred onto nitrocellulose membrane. To prevent the non-specific antibody conjugation on the nitrocellulose membrane, blocking was performed for 1 hour. Then, the membrane was washed twice with PBS. The membrane was reacted with R-catenin and ALP primary antibodies by stirring at room temperature for 2 hours. The membrane was washed with PBS 2~3 times. The membrane was reacted with HRP-conjugated secondary antibody diluted at the same ratio as the above, followed by reaction at room temperature for 2 hours. The expression amount of each protein was investigated by developing X-ray film.

As a result, as shown in FIG. 2, the expressions of β-catenin and ALP were increased in the skin cells treated with the centipede grass ethyl acetate fraction (A) or butanol fraction (B), compared with the control (Con) treated with distilled water (FIG. 2).

Experimental Example 3: Confirmation of Hair Growth Inducing Effect in Alopecia Induced Mouse <3-1> Confirmation of Hair Growth The following experiment was performed to investigate the hair growth inducing effect of the centipede grass ethyl acetate and butanol fractions distributed on the mouse skin with alopecia.

Particularly, 43 day old C57BL/6CrN mice (Central Lab. Animal Inc., Seoul) were adapted to a laboratory for 6 days. So, the 49 day old mice were used for this experiment. The mice were raised in an animal room at the constant temperature of 23±3° C. with the humidity of 55±3%. Each mouse cage contained three mice. The mice were grouped randomly for the experimental groups. During the experiment, the mice were provided with water and feed freely.

To apply the rest period of the hair growth cycle, the mouse back hair was primarily removed by using an electric razor carefully without damaging the skin. To remove hair follicles and tiny hairs in the skin secondarily, Niclean hair removal cream (Ildong Pharmaceutical Co., Ltd., Korea) containing thioglycolic acid was distributed on the skin, and then the inventors waited for 2 minutes to be absorbed well on the skin. Thereafter, the hair removal cream was removed with warm water, and 24 hours were given to the mice for recovery before the experiment. The mice were continuously observed and confirmed to have no inflammation. 0.2 ml of the sample was sprayed on the area where hair was removed once a day at 2 pm everyday for 21 days. At this time, a brush was used to spread the sample evenly. The negative control (DW) was treated with distilled water and the positive control (3% MXD) was treated with 3% Minoxidil (Dongsung Bio Pharm. Co., Ltd., Korea). The experimental group was treated with the centipede grass ethyl acetate fraction (A) and butanol fraction (B) (FIG. 3).

As a result, as shown in FIG. 4, dark blue skin color was observed in the negative control 10 days after the application. A partial hair growth was observed in the area where hair was removed, 18 days after the application. In the meantime, alopecia area was expanded 10 days after the application in the positive control group, wherein skin tone turned into dark blue. The general hair growth was observed in the center area where hair was removed, 21 days after the application. In the mice treated with the centipede grass ethyl acetate fraction (A) or butanol fraction (B), dark blue skin color was observed partially outer boundary of alopecia area 10 days after the application, and hair growth was clearly observed in about 90% of the whole of alopecia area 18 days after the application (FIG. 4).

<3-2> Confirmation of ALP Enzyme Activity in Skin Tissue

The following experiment was performed to investigate the effect of the centipede grass ethyl acetate and butanol fractions on ALP enzyme activity in mouse skin tissues.

Particularly, the skin was taken off from the back of the mouse treated with the sample for 21 days by the same manner as described in experimental example <3-1>, which was rapid-frozen in liquid nitrogen. 1 g of the skin was put into four times the skin weight of 0.1 M phosphate buffer solution, followed by homogenization. The homogenate was centrifuged at 12,000 rpm at 4° C. for 20 minutes. The obtained supernatant was used for the ALP enzyme activity measurement. The ALP enzyme activity was analyzed by the conventional method using an automatic biochemical analyzer (Hitachi-747).

As a result, as shown in FIG. 5, the ALP activity was higher in the group treated with the centipede grass ethyl acetate fraction (A) or butanol fraction (B) than in the negative control group (DW) (FIG. 5).

<3-3> Confirmation of IGF-1 Expression Level in Skin Tissue

The following experiment was performed to investigate the effect of the centipede grass ethyl acetate and butanol fractions on the IGF-1 mRNA expression in the mouse skin tissues.

Particularly, the skin was taken off from the back of the mouse treated with the sample for 20 days by the same manner as described in experimental example <3-1> to obtain the skin tissues. Skin tissue mRNA was extracted by the conventional method. qPCR (quantitative Real-time PCR) was performed with the sample by the conventional method, and the expression of IGF-1 mRNA was quantified by numerization of the signal. The relative level of IGF-I was normalized to $\beta$-actin As a result, as shown in FIG. 6, the expression of IGF-1 mRNA was increased 55% in the positive control (3% MXD), 33% in the experimental group treated with the centipede grass ethyl acetate fraction (A), and 42% in the experimental group treated with the centipede grass butanol fraction (B), compared with the negative control (DW) ($P<0.05$). That is, the IGF-1 mRNA expression levels were in the order of positive control> fraction B> fraction A>negative control, and the IGF-1 mRNA expression amount was increased with hair growth (FIG. 6).

<3-4> Confirmation of TGF-$\beta$ Expression Level in Skin Tissue

QPCR was performed by the same manner as described in experimental example <3-3> in order to investigate the effect of the centipede grass ethyl acetate and butanol fractions on the TGF-$\beta$ mRNA expression in the mouse skin tissues.

As a result, as shown in FIG. 7, the expression of TGF-1 mRNA was decreased 28% in the positive control (3% MXD), 25% in the experimental group treated with the centipede grass ethyl acetate fraction (A), and 19% in the experimental group treated with the centipede grass butanol fraction (B), compared with the negative control (DW) ($P<0.05$). That is, the TGF-5 mRNA expression levels were in the order of fraction A<positive control<fraction B<negative control, and the TGF-$\beta$ mRNA expression amount was decreased with hair growth (FIG. 7).

<3-5> Confirmation of Hair Follicle Growth in Skin Tissue

In the course of hair growth, melanin synthesis begins and thus the dermis layer becomes thicker and the size of hair follicle grows deep down to dermis and subcutaneous fat. The following experiment was performed to investigate the effect of the centipede grass ethyl acetate and butanol fractions on the growth of hair follicles.

Particularly, the skin was taken off from the back of the mouse treated with the sample for 21 days by the same manner as described in experimental example <3-1> to obtain the skin tissues. The obtained skin tissues were fixed in 4% neutral buffered paraformaldehyde for 48~72 hours. The fixed tissues were washed to eliminate the fixative, and reacted in 70% ethanol for 1 hour, in 80% ethanol for 1 hour, in 90% ethanol for 1 hour, in 95% ethanol for 1 hour, in 100% ethanol for 2 hours, and in xylene for 2 hours for dehydration and clarification, followed by embedding in paraffin using an embedding apparatus (Leica, Germany). The embedded paraffin block was cut into 5 Lm thick sections. The sections were reacted in xylene for 15 minutes twice, in 100% ethanol for 3 minutes, in 95% ethanol for 3 minutes, in 90% ethanol for 3 minutes, in 80% ethanol for 3 minutes, and in 70% ethanol for 3 minutes for deparaffinization and hydration. The tissues were stained with hematoxylin for 5 minutes and then with eosin for 1 minute. The tissues were enveloped by using permount, and the stained tissues were observed under optical microscope.

As a result, as shown in FIG. 8, the number of hair follicles and the depth of the same (thickness of dermis) were significantly increased in the positive control (3% MXD) and in the experimental group treated with the centipede grass ethyl acetate fraction (A) or the butanol fraction (B), compared with the negative control (DW). The number of hair follicles was increased, compared with the negative control, in the following order: fraction A<fraction B<positive control. The thickness of dermis was also increased (FIG. 8).

<3-6> Comparison of the Number of Hairs Grown

The number of hairs grown in the mouse of experimental example <3-1> was counted under optical microscope by the conventional method for the comparison.

As a result, as shown in FIG. 9, the number of hairs grown in the positive control group (3% MXD) mouse and in the experimental group mouse treated with the centipede grass ethyl acetate fraction (A) or the butanol fraction (B) was significantly increased, compared with that of the negative control group (DW) mouse (FIG. 9).

Experimental Example 4: Confirmation of Hair Growth Inducing Effect in Genetically Hairless Nude Mouse <4-1> Confirmation of Hair Growth The following experiment was performed to investigate the hair growth inducing effect of the centipede grass extract distributed on the genetically hairless nude mouse.

Particularly, 35 day old nude mice (CAnN.Cg-Foxn1nu, Orientibio, Seoul) were adapted to a laboratory for 6 days. So, the 41 day old mice were used for this experiment. The mice were raised in an animal room at the constant temperature of 23±3° C. with the humidity of 55±3%. Each mouse cage contained three mice. The mice were grouped randomly for the experimental groups. During the experiment, the mice were provided with water and feed freely. 0.2 ml of the sample was sprayed on the area where hair was removed once a day at 2 pm everyday for 30 days. At this time, a brush was used to spread the sample evenly. The negative control(A) was treated with distilled water and the experimental group(B) was treated with the centipede grass extract.

As a result, as shown in FIG. 10, the general hair growth was observed in the experimental group, 20 days after the application. After 30 days of application, it was observed that the hair growth was remarkably occurred in the entire back region. There was no change in the negative control group(FIG. 10).

<4-2> Confirmation of Hair Follicle Growth in the Skin Tissue the skin was taken off from the back of the mouse treated with the sample for 21 days by the same manner as described in experimental example <4-1> to obtain the skin tissues. The obtained skin tissues were fixed in 4% neutral buffered paraformaldehyde for 48~72 hours. The fixed tissues were washed to eliminate the fixative, and reacted in 70% ethanol for 1 hour, in 80% ethanol for 1 hour, in 90 ethanol for 1 hour, in 95% ethanol for 1 hour, in 100% ethanol for 2 hours, and in xylene for 2 hours for dehydration and clarification, followed by embedding in paraffin using an embedding apparatus (Leica, Germany). The embedded paraffin block was cut into 5 μm thick sections. The sections were reacted in xylene for 15 minutes twice, in 100% ethanol for 3 minutes, in 95% ethanol for 3 minutes, in 90% ethanol for 3 minutes, in 80% ethanol for 3 minutes, and in 70% ethanol for 3 minutes for deparaffinization and hydration. The tissues were stained with hematoxylin for 5 minutes and then with eosin for 1 minute. The tissues were enveloped by using permount, and the stained tissues were observed under optical microscope.

As a result, as shown in FIG. 11, the number of hair follicles and the depth of the same (thickness of dermis) were significantly increased in the experimental group(B) treated with the centipede grass extract, compared with the negative control(A). The number of hair follicles was increased in the experimental group, compared with the negative control. The thickness of dermis was also increased (FIG. 11).

<4-3> Comparison of the Number of Hairs Grown

The number of hairs grown in the mouse of experimental example <4-1> was counted under optical microscope by the conventional method for the comparison.

As a result, as shown in FIG. 12, the number of hairs grown in the experimental group(B) mouse treated with the centipede grass extract was significantly increased, compared with that of the negative control group(A) mouse (FIG. 12).

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for preventing or treating alopecia in a subject in need thereof, comprising administering a pharmaceutically effective dose of a fraction of a centipede grass (*Eremochloa ophiuroides*) extract,
   wherein the extract is prepared by a method comprising the steps of:
   (a) extracting centipede grass leaves with methanol to produce a methanol extract,
   (b) concentrating the methanol extract and suspending it in water to produce a suspension,
   (c) adding n-hexane to the suspension to yield a soluble layer and a water layer, then discarding the soluble layer,
   (d) combining the water layer with ethyl acetate to produce an ethyl acetate fraction, and
   (e) mixing the ethyl acetate fraction with 50-70% methanol to obtain a mixture, and subjecting the mixture to column chromatography to obtain the centipede grass extract.

2. A method for improving alopecia comprising administering a health functional food as an active ingredient to a subject in need thereof, wherein the health functional food is prepared by adding an effective amount of a fraction of a centipede grass extract,
   wherein the extract is prepared by a method comprising the steps of:
   (a) extracting centipede grass leaves with methanol to produce a methanol extract,
   (b) concentrating the methanol extract and suspending it in water to produce a suspension,
   (c) adding n-hexane to the suspension to yield a soluble layer and a water layer, then discarding the soluble layer, (d) combining the water layer with ethyl acetate to produce an ethyl acetate fraction, and
(e) mixing the ethyl acetate fraction with 50-70% methanol to obtain a mixture, and subjecting the mixture to column chromatography to obtain the centipede grass extract.

* * * * *